US008684973B2

(12) United States Patent
Cassemeyer et al.

(10) Patent No.: US 8,684,973 B2
(45) Date of Patent: Apr. 1, 2014

(54) MICROPUMP

(75) Inventors: Julia Cassemeyer, Reutlingen (DE); Ralph Reichenbach, Esslingen (DE)

(73) Assignee: Robert Bosch GmbH, Stuttgart (DE)

( * ) Notice: Subject to any disclaimer, the term of this patent is extended or adjusted under 35 U.S.C. 154(b) by 178 days.

(21) Appl. No.: 12/537,703

(22) Filed: Aug. 7, 2009

(65) Prior Publication Data

US 2010/0057006 A1 Mar. 4, 2010

(30) Foreign Application Priority Data

Aug. 26, 2008 (DE) .......................... 10 2008 041 542

(51) Int. Cl.
*A61M 1/00* (2006.01)
(52) U.S. Cl.
USPC ......................................... 604/153; 604/133
(58) Field of Classification Search
USPC ................ 604/131, 153, 134–139; 417/413.1
See application file for complete search history.

(56) References Cited

U.S. PATENT DOCUMENTS

| 3,209,721 | A | * | 10/1965 | Pall et al. ...................... 116/267 |
| 4,152,098 | A | * | 5/1979 | Moody et al. .............. 417/413.1 |
| 5,603,354 | A | * | 2/1997 | Jacobsen et al. ......... 137/625.48 |
| 5,647,575 | A | | 7/1997 | Jacobsen et al. |
| 5,839,467 | A | * | 11/1998 | Saaski et al. .................. 137/501 |
| 6,203,291 | B1 | * | 3/2001 | Stemme et al. ............ 417/413.3 |
| 2006/0195046 | A1 | * | 8/2006 | Sterling et al. ................ 600/583 |

FOREIGN PATENT DOCUMENTS

| DE | 102008003792 | 7/2009 |
| WO | WO 94/19609 | 9/1994 |
| WO | WO 2009/087025 | 7/2009 |

* cited by examiner

*Primary Examiner* — Jason Flick
*Assistant Examiner* — Melissa A Snyder
(74) *Attorney, Agent, or Firm* — Kenyon & Kenyon LLP

(57) ABSTRACT

A micropump, which in particular is a pump for a medicinal active substance and which may be an insulin pump or an analgesic pump, has at least one valve, which has a valve chamber, and has a pump chamber. At least one immobile structural element, which reduces the valve chamber volume, is provided in the valve chamber.

22 Claims, 5 Drawing Sheets ically known. However, micropumps
MICROPUMP

FIELD OF THE INVENTION

The present invention relates to a micropump, in particular for delivering medicinal active substances such as insulin or analgesics.

BACKGROUND INFORMATION

Micropumps for the controlled and high-precision delivery of insulin are fundamentally known. However, micropumps up to this point are adversely affected by complex manufacturing processes having many nonstandard processing steps. The many special processing steps according to the previous related art make micropumps of this type costly and lower the manufacturing yields.

In addition, known micropumps are not sufficiently precise in regard to the delivered active substance quantities. Micropumps for insulin delivery must operate very precisely at high dosing precision, however, without complex sensors for detecting delivered insulin quantities. An active flow measurement is very problematic in connection with insulin, because the substance reacts to increased temperatures by being damaged, for example, in connection with so-called hot film sensors for flow measurement.

A grave disadvantage of micropumps up to this point is additionally the lack of safety: thus, for example, in micropumps according to the previous related art, the delivered insulin quantity is a function of the pre-pressure in the insulin supply container, which may be placed under mechanical pressure if it is designed as a flexible bag. For example, if the pump wearer of the insulin micropump sits or lies on the supply container, this may result in an unintentional insulin delivery or an unintentional increase of the dose just delivered. In view of the hazard of an insulin overdose, this is to be avoided under all circumstances.

Therefore, an improved micropump for insulin delivery has been developed by the applicant. An application for a patent for this micropump was made with the application DE 10 2008 00 37 92.3, which is not yet published as of the filing date of the present application. The improved micropump is distinguished in that the functional elements of the micropump are exclusively manufactured by structuring from one direction, whereby fragile intermediate states are avoided in the manufacturing of the micropump, so that support films, etc., may in turn be dispensed with during the manufacturing and thus the requirements for large-scale manufacturing of the micropump are provided.

Efforts have been made to optimize micropumps in such a way that they are capable of self-priming and are tolerant of gas bubbles.

SUMMARY OF THE INVENTION

The exemplary embodiments and/or exemplary methods of the present invention is based on the object of proposing a micropump which is capable of self-priming and is tolerant of gas bubbles, in particular for medicinal active substance delivery, which may be for insulin delivery.

This object is achieved by a micropump having the features described herein. Advantageous refinements of the exemplary embodiments and/or exemplary methods of the present invention are specified in the subclaims. All combinations of at least two features disclosed in the description, the claims, and/or the figures are within the scope of the exemplary embodiments and/or exemplary methods of the present invention.

The exemplary embodiments and/or exemplary methods of the present invention has recognized that the compression ratio of a micropump is a measure of the tolerance of the micropump with respect to gas bubbles and, furthermore, the capability of the micropump of priming itself. The compression ratio of a micropump is the ratio of the active pump volume to the total volume of the pump or, in other words, the ratio of active pump volume to the sum of active pump volume and dead volume.

To achieve the greatest possible compression ratio and a gas bubble tolerance and self-priming capability connected thereto, the exemplary embodiments and/or exemplary methods of the present invention proposes reducing the dead volume of a micropump in that, in a valve chamber of at least one valve of the micropump, at least one immobile structural element, which reduces the valve chamber volume, is provided. In other words, the exemplary embodiments and/or exemplary methods of the present invention is based on the idea of reducing the dead volume of the micropump by providing at least one structural element in the area of a valve chamber, the structural element decreasing the volume of the valve chamber in comparison to a micropump without the structural element.

Through a corresponding reduction of the dead volume, it is possible that the micropump may also pump compressible media such as gases, for example, air. Through the immobile placement of the at least one structural element, only the dead volume is decreased, which does not influence the rigidity of the appropriately designed valve or its functionality in any way, however. A specific embodiment of the micropump may particularly be used in which both at least one inlet valve and also at least one outlet valve, very particularly which may be all valves, is/are designed as valves designed according to the concept of the exemplary embodiments and/or exemplary methods of the present invention having at least one immobile structural element which reduces the valve chamber volume (dead volume). The type or the shape of the structural element may fundamentally be selected freely. The at least one structural element may be designed as large as possible, in order to decrease the dead volume as strongly as possible, without exerting any negative or undesired influence on the functionality and the reliability of the valve.

In a refinement of the exemplary embodiments and/or exemplary methods of the present invention, it is advantageously provided that the at least one structural element is provided with an antistick coating on a side which delimits the valve chamber and faces toward the diaphragm and/or a free space is provided between a diaphragm of this type and the structural element. Because the structural element is not connected to the diaphragm or designed to be a single piece therewith, the inertia of the system is not unnecessarily elevated, which has a positive effect on the dynamics of the valve. Higher mechanical tensions might arise due to a diaphragm stiffened by a structural element, which may even result in the extreme case in a failure fracture of the diaphragm.

In a refinement of the exemplary embodiments and/or exemplary methods of the present invention, it is advantageously provided that an antistick coating is also provided on a side of the structural element which faces away from the diaphragm, or a spacing is implemented to a carrier layer of the micropump, which is rigid in particular. In other words, a specific embodiment may be used in which the height of the valve chamber along the displacement axis of a valve element is greater than the extension of the structural element in this direction.

However, a specific embodiment may also be implemented in which the at least one structural element is formed by the carrier layer or is fixed thereon. It is essential that the structural element is not connected to the diaphragm diametrically opposite to the carrier layer or designed to be a single piece therewith.

A specific embodiment of the micropump very particularly may be used in which the at least one structural element is situated in an area between a peripheral wall, which externally delimits the valve chamber and may be in the form of the inside of a hollow cylinder, and an adjustable valve element, which is particularly implemented as a valve plunger. The structural element may maintain a spacing to the valve element, which is designed in particular as a valve plunger, in order not to negatively influence the dynamics of the system by the additional moving mass.

A specific embodiment of the micropump very particularly may be used in which the at least one structural element, which minimizes the dead volume, is fixedly connected to the peripheral wall, which radially externally delimits the valve chamber, or is designed to be a single piece therewith, whereby an especially robust valve is obtained.

It is expedient in particular if a channel, in particular designed as an annular channel, is formed radially between the at least one structural element, which may be between the multiple structural elements situated adjacent to one another around the circumference, and the valve element, through which the medium to be conveyed—depending on the design of the valve as an inlet valve or an outlet valve—may flow into the valve or out of the valve, respectively.

A specific embodiment of the micropump very particularly may be used in which the valve element, which may be designed as a valve plunger (valve piston), is elastically suspended using at least one spring, which is designed in particular as a coiled spring. Multiple coiled springs situated adjacent to one another around the circumference very particularly may be provided, using which the valve element is fixed or elastically mounted laterally on a peripheral wall of the valve chamber.

So as not to negatively influence the dynamics of an elastically suspended valve element, in a refinement of the exemplary embodiments and/or exemplary methods of the present invention, it is advantageously provided that the at least one structural element is situated at a distance to the at least one coiled spring. A specific embodiment particularly may be used in which the at least one structural element is situated between two coiled springs, which are adjacent in the peripheral direction. Very particularly, multiple structural elements may be provided, at least one, which may be exclusively one coiled spring, which may connect the valve element to the inner peripheral wall of the valve chamber, being situated between each two structural elements which are adjacent in the peripheral direction. Very particularly, the valve having the valve element spring-mounted via a coiled spring may be an inlet valve of the micropump.

In order to not obstruct the flow through the micropump, i.e., the inflow and outflow of a medium to be conveyed, in the direction toward the valve or in the direction away from the valve, it is advantageously provided in a refinement of the exemplary embodiments and/or exemplary methods of the present invention that the at least one structural element is not situated inside the inflow or outflow area of the valve chamber; the inflow or outflow area of the valve chamber is thus designed free of structural elements.

A specific embodiment of the micropump very particularly may be used in which the at least one valve having a structural element is designed as an inlet valve. Additionally or alternatively, it is advantageous if a valve provided with a structural element is designed as an outlet valve.

In a refinement of the exemplary embodiments and/or exemplary methods of the present invention it is advantageously provided that all functional elements of the micropump are exclusively produced by structuring from one direction. In other words, the micropump is produced by structuring, in particular of semiconductor material, which may be by etching, from only one direction. The structuring may be performed starting from a front side of a carrier layer. In still other words, it is proposed to manufacture the micropump by providing at least one integral carrier, namely a first carrier layer, on whose front side multiple layers are situated, at least one layer of which being structured to manufacture the functional elements, such as the valves and/or the at least one diaphragm, and not from the rear side of the carrier layer, which may be used as the support, but rather from the front side of the carrier layer in the direction toward the first carrier layer.

The first carrier layer may remain unstructured during the manufacturing of the functional elements and thus ensures absolute tightness between the front side of the first carrier layer and the rear side of the carrier layer, using which the carrier layer always rests on a so-called chuck of a processing station or facility during the manufacturing of the micropump. The carrier layer may be removed before the micropump is finished. Because the carrier layer is present, which may be undamaged, during the production of the functional elements, fragile intermediate stages are advantageously avoided during the manufacturing of the micropump, whereby support films, etc., may be dispensed with during the manufacturing and the condition for large-scale manufacturing of the micropump is thus provided. Very particularly, the micropump may be designed as in German patent document DE 10 2008 00 37 92.3 (which is not a prior publication). The content of the disclosure of the above-mentioned patent application is to be considered as disclosed associated with the present patent application in such a way that at least one arbitrary feature of the present application may be combined and claimed with at least one arbitrary feature from German patent document DE 10 2008 00 37 92.3.

Further advantages, features, and details of the exemplary embodiments and/or exemplary methods of the present invention result from the following description of exemplary embodiments and on the basis of the drawings.

DETAILED DESCRIPTION

Figure 1:
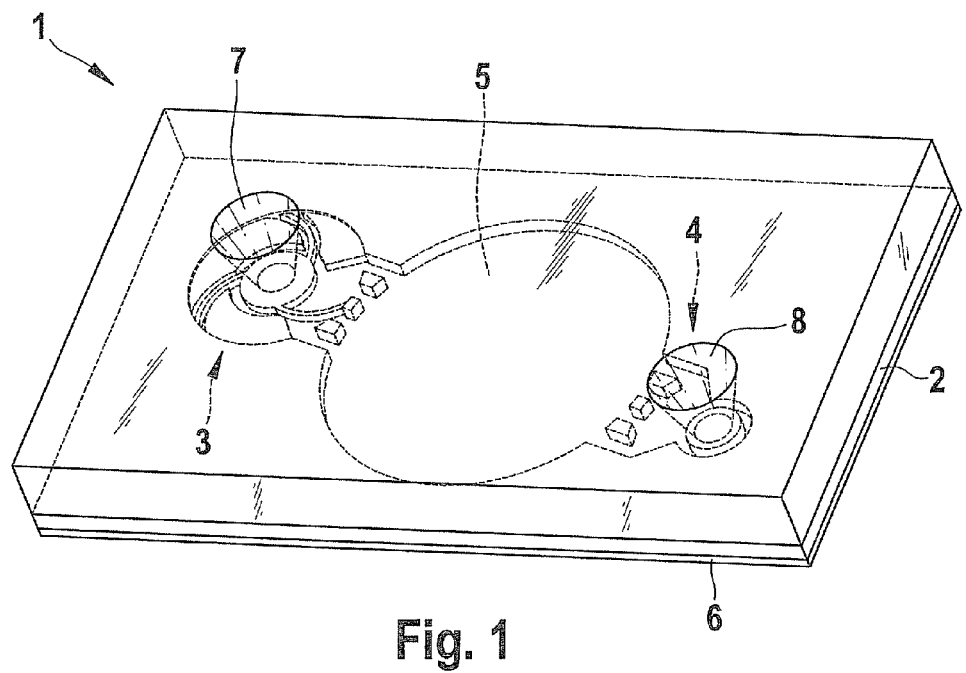
FIG. 1 shows a perspective, incomplete illustration of the essential elements of a micropump, including an inlet valve, a pump chamber, and an outlet valve.

Identical elements and elements having identical functions are identified using identical reference numerals in the figures.

Figure 2:
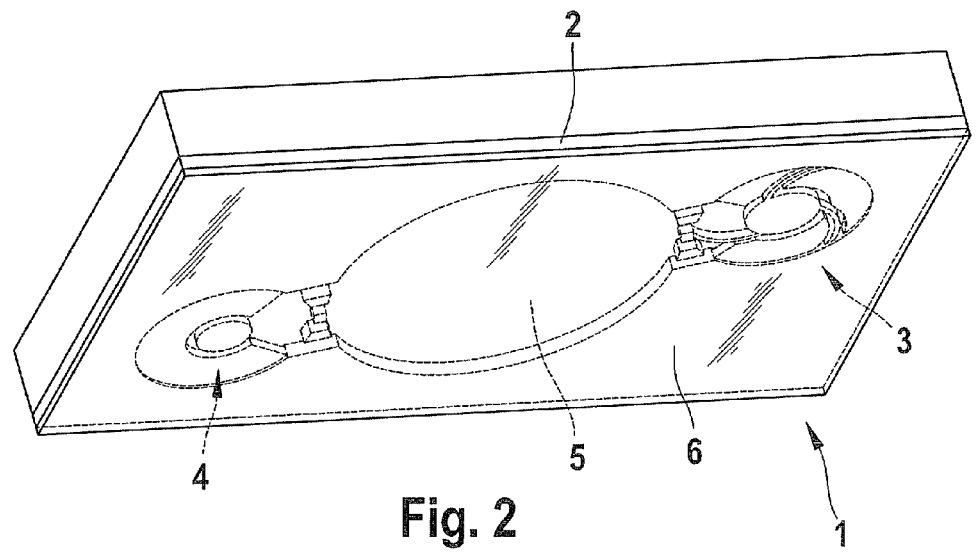
FIG. 2 shows an illustration of the essential elements of the micropump according to FIG. 1 in a view from below.

A micropump 1, which is designed as an insulin pump, is shown in an incomplete illustration in FIGS. 1 and 2. A functional layer 2 may be seen, which is approximately 15 µm to 24 µm thick, and in which multiple functional elements of micropump 1 are implemented in the form of a first valve 3, designed as an inlet valve, and in the form of a second valve 4, designed as an outlet valve. A pump chamber 5 is located in an area between the two valves 3, 4. Valves 3, 4 and pump chamber 5 are delimited on the bottom in FIG. 1 by a base layer used as a diaphragm 6, which is shown in FIG. 2 in a view from below and which is shown as transparent in an area below valves 3, 4 and below pump chamber 5 in FIG. 2 for better understanding. To operate micropump 1, an actuator, designed in particular as a piezostack, may be located in each case in an area below diaphragm 6 under the valves and below pump chamber 5, a specific embodiment also being able to be designed in which an actuator is associated exclusively with first valve 3 and pump chamber 5 in each case. In regard to the activation options which may be implemented, reference is hereby made to German patent document DE 10 2008 00 37 92.3 (which is incorporated by reference, and which is not a prior publication).

On the side of functional layer 2 facing away from diaphragm 6, in micropump 1, a second carrier layer (not shown for reasons of clarity) is located, which is penetrated by a schematically shown inlet channel 7 for supplying first valve 3 with insulin and by an outlet channel 8 for letting out insulin flowing out of second valve 4. A first carrier layer (also not shown) and a stop layer located on this first carrier layer were removed after the manufacturing of micropump 1. The manufacturing was performed starting from the first carrier layer, formed by a silicon wafer, in the direction of the second carrier layer (not shown for reasons of clarity).

The construction of first valve 3, which is designed as an inlet valve, is explained hereafter on the basis of FIGS. 3 through 4, in FIG. 4, which shows first valve 3 in a view from below, the illustration of diaphragm 6 having been dispensed with below first valve chamber 9 of first valve 3 and in an area below pump chamber 5 for better understanding. A central first valve element, which is designed as a cylindrical valve plunger, and which is not fixedly connected to diaphragm 6, but rather is movable in relation thereto, may be seen. First valve element 10 is suspended with the aid of three coiled springs 11, which are distributed uniformly around the circumference and, on the one hand, on an inner first peripheral wall 12, in the form of an inner surface of a hollow cylinder of first valve 3, and on a structure 13 for regulating the medium flow from first valve chamber 9 into pump chamber 5. Starting from first valve element 10, coiled springs 11 extend both in the radial direction and in the peripheral direction.

The valve chamber volume of first valve chamber 9, i.e., the dead volume of micropump 1, is minimized by a total of three first structural elements 14, which are situated in an area between first peripheral wall 12 and first valve element 10. In the present case, structural elements 14 are designed to be a single piece with first peripheral wall 12, i.e., from the same layer, and extend starting therefrom inward in the radial direction, a spacing in the form of a channel remaining between the inner circumference of first structural elements 14 and the outer circumference of valve element 10. It may also be seen that first structural elements 14 are situated at a distance to coiled springs 11, which each extend in the radial direction through the area between two first structural elements 14 up to inner peripheral wall 12. As may also be seen from FIG. 4, each first structural element 14 is situated between two coiled springs 11, which are adjacent in the peripheral direction.

Figure 3:
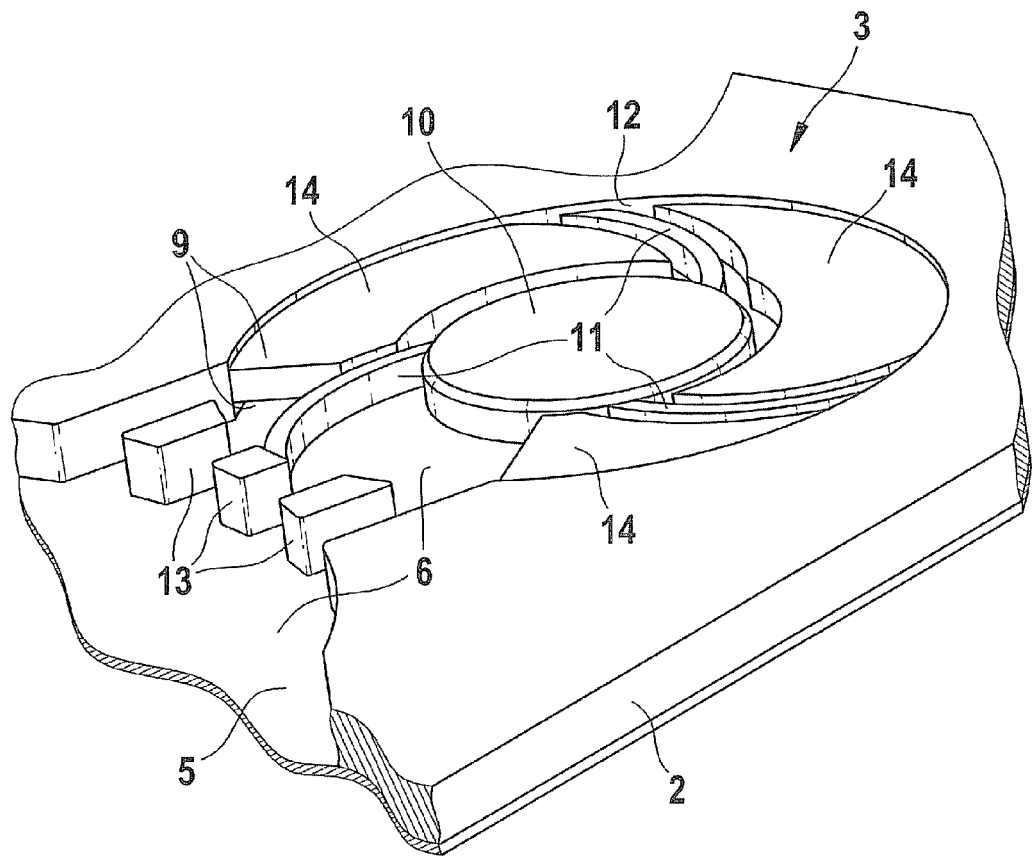
FIG. 3 shows an enlarged illustration of the inlet valve according to FIGS. 1 and 2 in a view from above.
Figure 4:
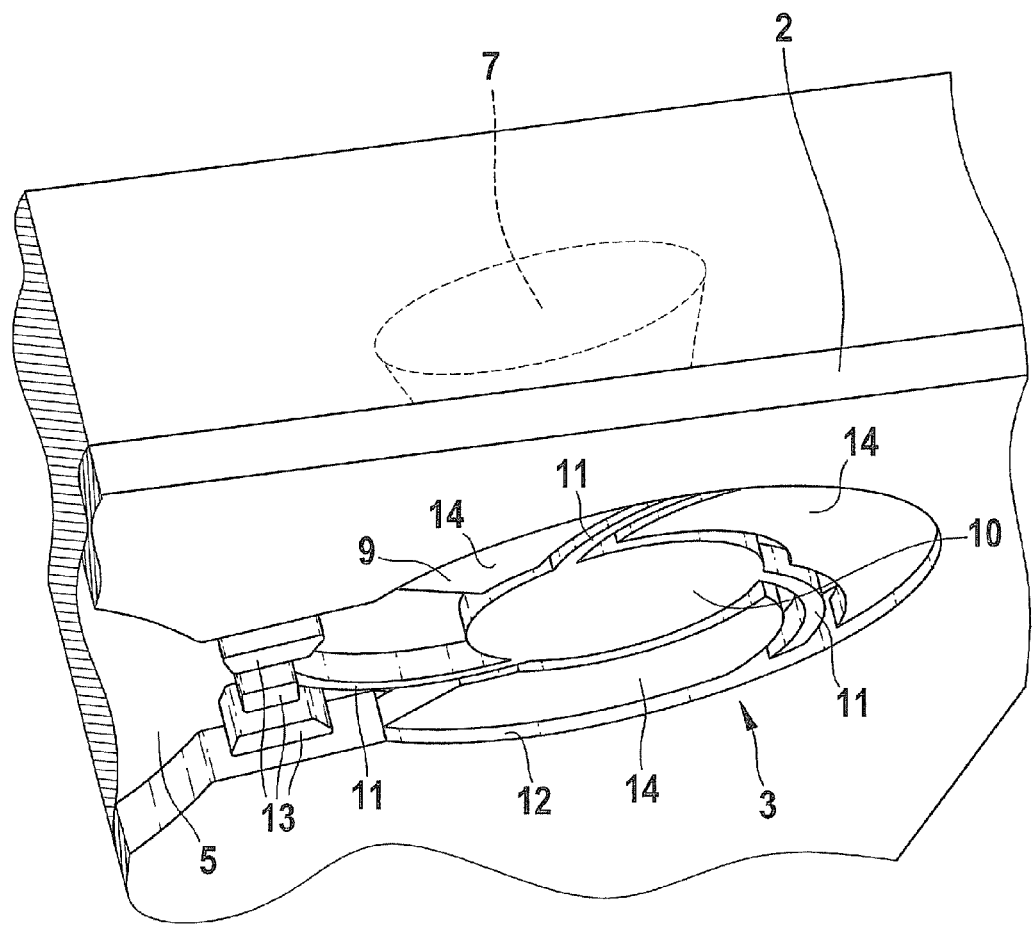
FIG. 4 shows a view of the inlet valve from below.
Figure 5:
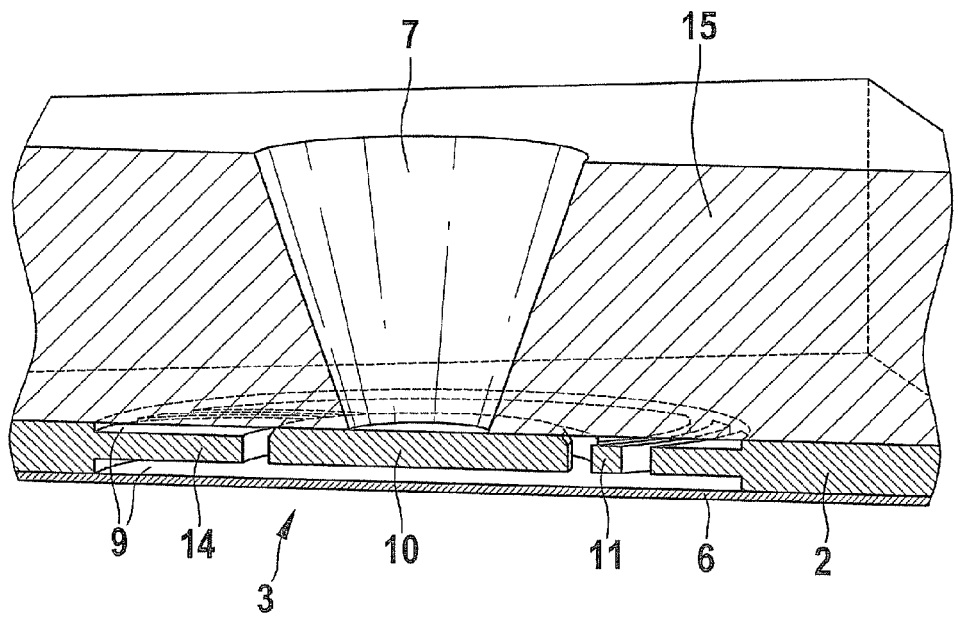
FIG. 5 shows a sectional illustration of the inlet valve.

It may be seen by considering FIGS. 3 and 4 together that first structural elements 14 do not rest on diaphragm 6, but rather are situated at a distance thereto. First structural elements 14 are also spaced apart from the second carrier layer (not shown), so that first valve chamber 9 extends, starting from the channel formed between first structural elements 14 and first valve element 10, in the radial direction into areas above and below structural elements 14. This is particularly apparent from FIG. 5, which shows a second carrier layer 15, which forms a type of cover of micropump 1. Furthermore, it may be seen from FIG. 5 that carrier layer 15 is penetrated by inlet channel 7. Furthermore, it may be seen from FIG. 5 that both structural elements 14 and also first valve element 10 are spaced apart from diaphragm 6 in the idle position of micropump 1. An actuator, which is designed in particular as a piezostack, to be provided below diaphragm 6 is not shown.

Figure 6:
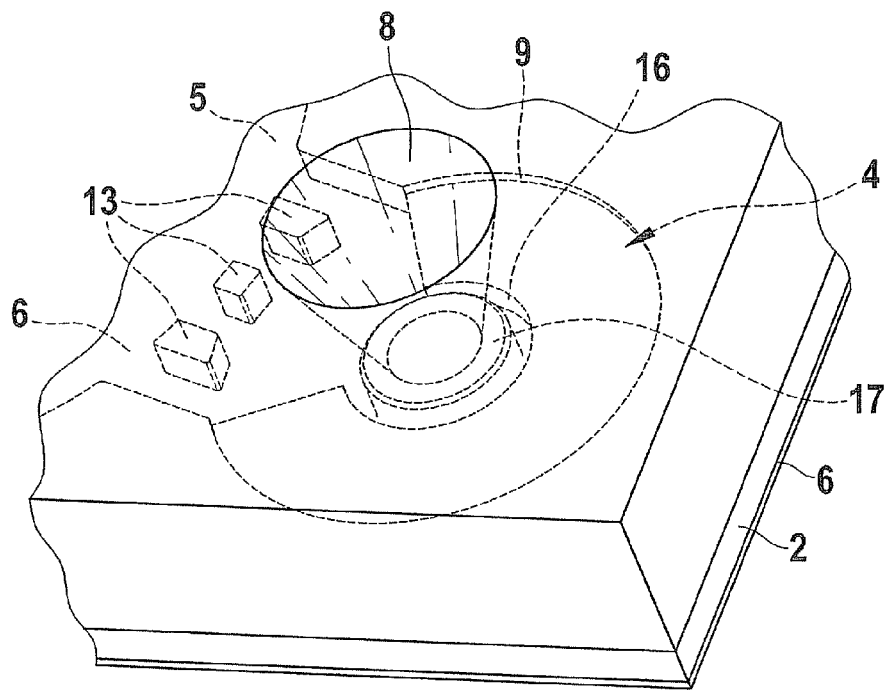
FIG. 6 shows a perspective illustration of the outlet valve of the micropump according to FIGS. 1 and 2 in a view from above.
Figure 7:
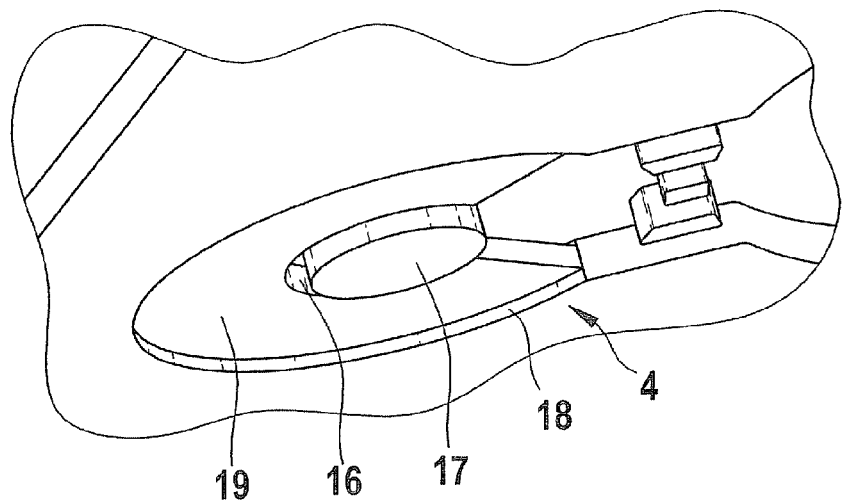
FIG. 7 shows an illustration of the outlet valve in a view from below.
Figure 8:
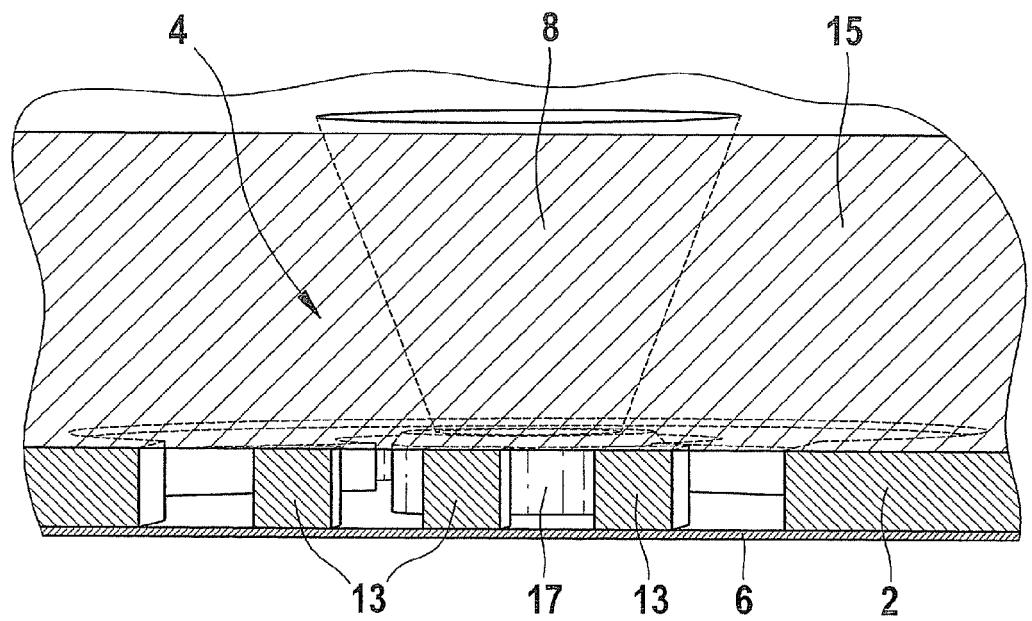
FIG. 8 shows a sectional illustration of the outlet valve.

Valve 4, which is shown in FIG. 2 and is used as an outlet valve, is shown in FIGS. 6 through 8. Structures 13 for flow regulation are also provided here between pump chamber 5 and a second valve chamber 16 of second valve 4. Structures 13 are fixedly connected to diaphragm 6. Furthermore, it may be seen that, as in the previously described inlet valve, the area between pump chamber 5 and second valve chamber 16 is free of immobile structural elements. The structures in front of second valve 4, which are shown in FIG. 6, are fixedly connected to diaphragm 6 like structures 13 in first valve 3, which is used as an inlet valve.

It may be seen by considering FIGS. 6 and 8 together that second carrier layer 15, which is exclusively shown in FIG. 8, is penetrated by outlet channel 8, through which the medium conveyed by micropump 1 is let out. As results from FIGS. 6 through 8, a second structural element 19 in the form of a circular ring segment is provided radially between a second valve element 17, which is designed as a cylindrical valve plunger, and a second inner peripheral wall 18 of second valve chamber 16 to decrease the dead volume of second valve 4. Second structural element 19 is situated like first structural elements 14 in such a way that a channel, an annular channel here, remains between the valve element, second valve element 17 here, and second structural element 19. Second structural element 19 is situated at a distance to diaphragm 6 and directly adjoins second carrier layer 15 on the side facing away from diaphragm 6 (cf. FIG. 8). Second valve chamber 16 thus extends from the channel, which is designed as an annular channel, between second valve element 17 and second structural element 19 in the radial direction into an area below second structural element 19, i.e., into an area between second structural element 19 and diaphragm 6.

What is claimed is:

1. A micropump for a medicinal active substance, comprising:
    a pump arrangement; and
    at least one valve, in the pump arrangement, having a valve chamber and a pump chamber,
    wherein the valve chamber and the pump chamber are both situated in the same direction of flow of the medicinal active substance with respect to the at least one valve,
    wherein at least one immobile structural element, which reduces the valve chamber volume, is in the valve chamber, wherein the structural element, on a side facing toward or away from a moveable diaphragm which delimits the valve chamber, is situated at a distance to the diaphragm, and wherein the at least one immobile structural element is not situated in the pump chamber.

2. The micropump of claim 1, wherein the structural element, on a side facing toward or away from a movable diaphragm which delimits the valve chamber has an antistick coating.

3. The micropump of claim 1, wherein the structural element, on a side facing toward an immobile carrier layer which delimits the valve chamber, satisfies at least one of the following: (i) it has an antistick coating, and (ii) it is situated at a distance to the carrier layer.

4. The micropump of claim 1, wherein the structural element is situated in an area between a peripheral wall, which externally delimits the valve chamber, and an adjustable valve element, which is a valve plunger.

5. A micropump for a medicinal active substance, comprising:
a pump arrangement; and
at least one valve, in the pump arrangement, having a valve chamber and a pump chamber,
wherein the valve chamber and the pump chamber are both situated in the same direction of flow of the medicinal active substance with respect to the at least one valve,
wherein at least one immobile structural element, which reduces the valve chamber volume, is in the valve chamber,
wherein the structural element, on a side facing toward or away from a moveable diaphragm which delimits the valve chamber, is situated at a distance to the diaphragm,
wherein the structural element is situated in an area between a peripheral wall, which externally delimits the valve chamber, and an adjustable valve element, which is a valve plunger, and
wherein the structural element is connected to the peripheral wall or is an extension of the peripheral wall directed radially inward.

6. A micropump for a medicinal active substance, comprising:
a pump arrangement; and
at least one valve, in the pump arrangement, having a valve chamber and a pump chamber,
wherein the valve chamber and the pump chamber are both situated in the same direction of flow of the medicinal active substance with respect to the at least one valve,
wherein at least one immobile structural element, which reduces the valve chamber volume, is in the valve chamber,
wherein the structural element, on a side facing toward or away from a moveable diaphragm which delimits the valve chamber, is situated at a distance to the diaphragm,
wherein the structural element is situated in an area between a peripheral wall, which externally delimits the valve chamber, and an adjustable valve element, which is a valve plunger, and
wherein a channel, which is an annular channel, is formed radially between the structural element and the valve element.

7. A micropump for a medicinal active substance, comprising:
a pump arrangement; and
at least one valve, in the pump arrangement, having a valve chamber and a pump chamber, wherein the valve chamber and the pump chamber are both situated in the same direction of flow of the medicinal active substance with respect to the at least one valve,
wherein at least one immobile structural element, which reduces the valve chamber volume, is in the valve chamber,
wherein the structural element, on a side facing toward or away from a moveable diaphragm which delimits the valve chamber, is situated at a distance to the diaphragm, and
wherein the valve element is elastically suspended using at least one spring, which is a coiled spring.

8. The micropump of claim 7, wherein the structural element is situated between two coiled springs, which are adjacent in the peripheral direction.

9. The micropump of claim 7, wherein the structural element is situated at a distance to the coiled spring.

10. The micropump of claim 1, wherein the structural element is exclusively situated at a distance to an inflow area or an outflow area of the valve chamber.

11. The micropump of claim 1, wherein the at least one valve is an inlet valve.

12. The micropump of claim 1, wherein the at least one valve is an outlet valve.

13. The micropump of claim 1, wherein all functional elements of the micropump are exclusively manufactured by structuring from one direction.

14. The micropump of claim 1, wherein the micropump is an insulin pump.

15. The micropump of claim 1, wherein the micropump is an analgesic pump.

16. The micropump of claim 1, wherein the structural element is situated in an area between a peripheral wall, which externally delimits the valve chamber and is in the form of an internal wall of a hollow cylinder, and an adjustable valve element, which is a valve plunger.

17. The micropump of claim 1, wherein the structural element, on a side facing toward or away from a movable diaphragm which delimits the valve chamber has an antistick coating, wherein the structural element is exclusively situated at a distance to an inflow area or an outflow area of the valve chamber.

18. The micropump of claim 1, wherein the structural element, on a side facing toward an immobile carrier layer which delimits the valve chamber, satisfies at least one of the following: (i) it has an antistick coating, and (ii) it is situated at a distance to the carrier layer, wherein the structural element is exclusively situated at a distance to an inflow area or an outflow area of the valve chamber.

19. A micropump for a medicinal active substance, comprising:
a pump arrangement; and
at least one valve, in the pump arrangement, having a valve chamber and a pump chamber,
wherein the valve chamber and the pump chamber are both situated in the same direction of flow of the medicinal active substance with respect to the at least one valve,
wherein at least one immobile structural element, which reduces the valve chamber volume, is in the valve chamber,
wherein the structural element, on a side facing toward or away from a moveable diaphragm which delimits the valve chamber, is situated at a distance to the diaphragm, and
wherein the structural element is situated in an area between a peripheral wall, which externally delimits the valve chamber, and an adjustable valve element, which is a valve plunger, wherein the structural element is connected to the peripheral wall or is an extension of the peripheral wall directed radially inward, wherein a channel, which is an annular channel, is formed radially between the structural element and the valve element, wherein the valve element is elastically suspended using at least one spring, which is a coiled spring.

20. The micropump of claim 19, wherein the structural element is situated between two coiled springs, which are adjacent in the peripheral direction.

21. The micropump of claim 19, wherein the structural element is situated at a distance to the coiled spring.

22. The micropump of claim 19, wherein the structural element is exclusively situated at a distance to an inflow area or an outflow area of the valve chamber.

* * * * *